United States Patent [19]

Ranalli

[11] Patent Number: 4,590,935
[45] Date of Patent: May 27, 1986

[54] CONTROL SYSTEM FOR INTRAOCULAR SURGICAL DEVICE

[75] Inventor: Domenico Ranalli, Rome, Italy

[73] Assignee: Optikon Oftalmologia, S.p.A., Rome, Italy

[21] Appl. No.: 578,076

[22] Filed: Feb. 8, 1984

Related U.S. Application Data

[62] Division of Ser. No. 317,115, Nov. 2, 1981, Pat. No. 4,449,550.

[51] Int. Cl.⁴ .............................................. A61B 17/32
[52] U.S. Cl. ...................................... 128/305; 604/22
[58] Field of Search ......................... 128/305, 751–758; 604/22, 23; 136/896, 624.12–624.15

[56] References Cited

U.S. PATENT DOCUMENTS

| | | | |
|---|---|---|---|
| 3,033,194 | 5/1962 | Lippert | 604/22 |
| 3,126,889 | 3/1964 | Blumenfeld | 128/305 |
| 3,805,793 | 4/1974 | Wright | 128/305 |
| 3,815,604 | 6/1974 | O'Malley et al. | 604/22 |
| 3,884,238 | 5/1975 | O'Malley et al. | 604/22 |

*Primary Examiner*—Edward M. Coven
*Attorney, Agent, or Firm*—McAulay, Fields, Fisher, Goldstein & Nissen

[57] ABSTRACT

A control system for an intraocular surgical device has first and second actuatable one-way valves connected in series with a high pressure gas input, with the output of the second valve vented to the atmosphere and each valve being actuatable between a closed state and an open state wherein the input and output are in communication. A five-way actuatable valve has an input connected to the series connection between the first and second valves, two outputs vented to the atmosphere and two outputs connectable to a surgical device. The five-way valve is actuatable between a first state wherein the input is in communication with one device output and the other device output is in communication with one venting output and a second state wherein the input is in communication with the other device output and the one device output is in communication with the other venting output. A control circuit maintains the first and second valves in the closed and open states respectively until a device is connected and thereafter reverses said states and for selectively actuating the five-way valve between the first and second states only when the first valve is open and the second valve is closed.

1 Claim, 3 Drawing Figures

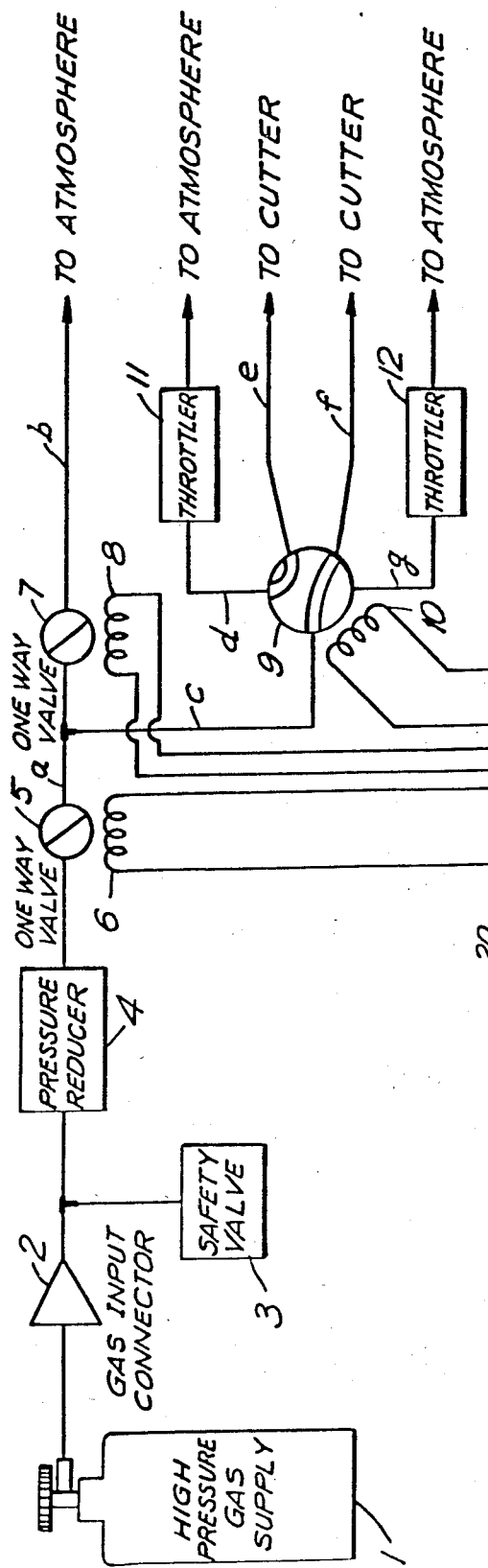
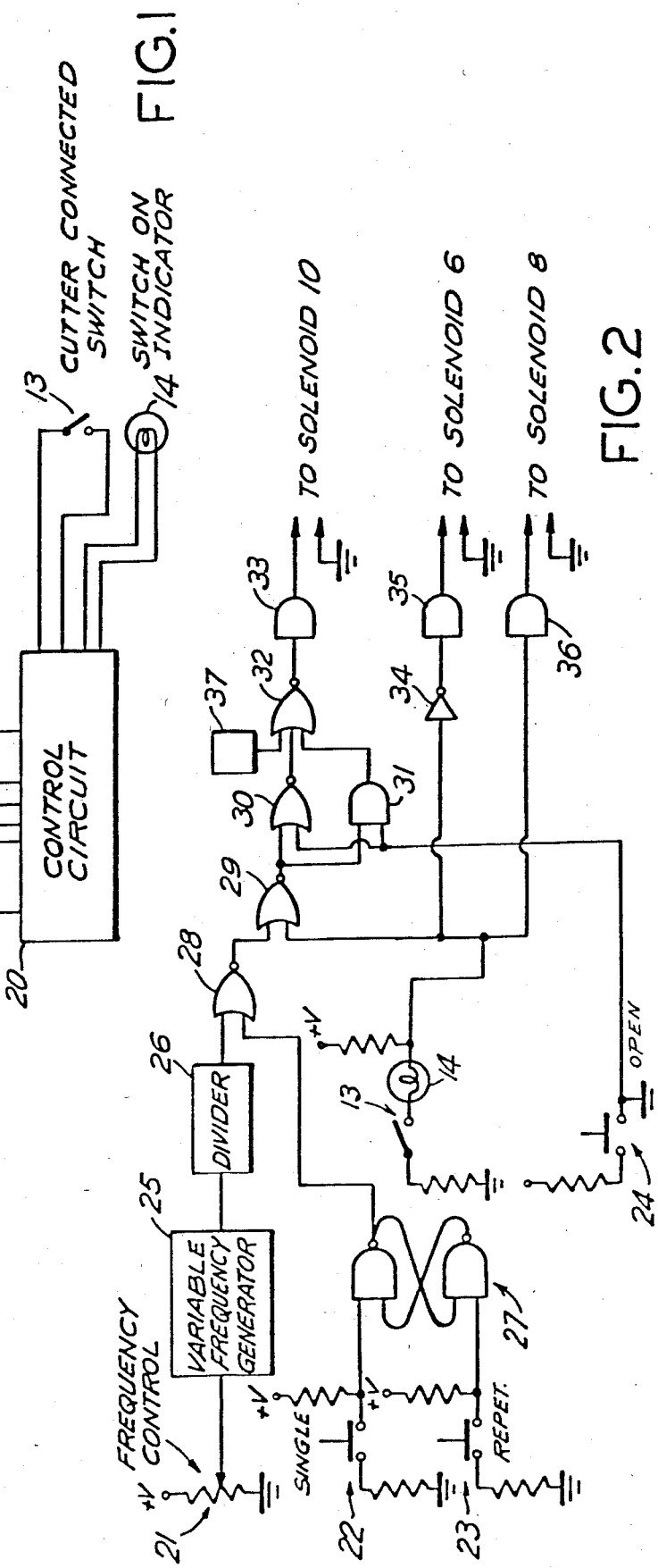
FIG.1
FIG.2

CONTROL SYSTEM FOR INTRAOCULAR SURGICAL DEVICE

This is a continuation of application Ser. No. 317,115, filed Nov. 2, 1981, now U.S. Pat. No. 4,449,550.

BACKGROUND OF THE INVENTION

The present invention relates to a control system for an intraocular surgical device and in particular for use with a device for vitrectomy.

Various devices have been proposed to cut and suck vitreous from the eye of a patient suffering from certain diseases, trauma or endoocular complications. Devices of this type are well known as vitreous cutters.

Vitreous cutters basically comprise a blade and a motor of either the electrical or pneumatic type which moves the blade. The control of the cutter is carried out by a control system which is in turn under the control of the opthamalogical surgeon.

While in the past the small vitreous cutters were activated by a small DC motor or by a magnetic solenoid, U.S. Pat. Nos. 3,815,604 and 3,884,238 disclosed a pneumatically activated cutter which made use of a gas under pressure to start the cutter in operation.

The pneumatic cutter constitutes a significant advance over the DC or magnetic solenoid actuated type, however it was found that the control systems disclosed in the aforementioned U.S. patents have several disadvantages which may cause problems during surgery.

For example, the control system disclosed therein requires a small compressor to be built into the console which developes only a few psi of positive pressure and vacuum for actuating the cutter. The cutting force is therefore very limited and during the surgery the blade may easily block causing problems for the surgeon.

Moreover, the blade must move back and forth to effect cutting and the movement in one direction is due to the positive pressure created by the compressor, while the movement in the other direction is created by the elastic action of the bellows and the depressure created by the compressor. As a result, the force which is used in the backward movement is very small and creates problems during surgery since the blade has its cutting action only when it is activated in the forward direction. This limits the type of blades which can be used.

SUMMARY OF THE INVENTION

The main object of the present invention is to provide a control system for an intraocular surgical device which eliminates the disadvantages of the prior art systems.

Another object of the present invention is to create a pneumatic control system permitting high cutting forces and permitting the use of pneumatic cutters which can accept blades of any kind, that is, cutting in the forward or backward direction and even microscissors which cut by repetitive blade action.

The basic principle of the control system according to the present invention is not to use any mechanical aid within the cutter itself for actuating the cutting action, but rather utilize a high pressure pneumatic force which is applied to the cutter to effect movement in either direction so that the blade thereof is actuated by the same force in either direction.

In this manner, a cutter operated by the control system in accordance with the invention is able to cut vitreous or any other endoocular structure like membranes, strands, lens, iris and so forth. Moreover, the control system according to the invention enables a vitreous cutter to be small, lightweight and still powerful in its ability to cut heavy endoocular structures. Additionally, this same cutter may be used wherever such high cutting face is required for such surgical procedures.

A further object of the control system according to the invention is to permit the operator to connect the system to push-cut or pull-cut blades.

In accordance with the present invention, a control system according to the invention includes gas input means repetitive of a supply of high pressure gas, that is, gas having a pressure of 750 psi which is optionally reduced down to approximately 150 psi. The gas is then fed to a first and a second actuatable one-way valve connected in series with the gas input means, with the input of the first valve connected to the output of the gas input means and the output of the second valve vented to the atmosphere. Each of the two valves has a closed state wherein the input and output thereof are not in communication and an open state wherein the input and output thereof are in communication. A five-way valve means having an input connected to the series connection between the first and second valves is provided with two outputs vented to the atmosphere and two outputs connectable to a surgical device. The five-way valve means has two states, a first state wherein the input is in communication with one device output and the other device output is in communication with one venting output and a second state wherein the input is in communication with the other device output and the one device output is in communication with the other venting output. All of the valves are controlled by control means which maintains the first and second valves in the closed and open states respectively until the device is connected to the system and thereafter reverses the states and selectively actuates the five-way valve between the first and second states only when the first valve is open and the second valve is closed.

These and other advantages of the present invention will become more apparent in connection with the detailed description of the preferred embodiments thereof and the attached drawings, wherein:

BRIEF DESCRIPTION OF THE DRAWINGS

FIG. 1 is a schematic diagram of the control system according to the present invention;

FIG. 2 is an electrical schematic of the control circuit of FIG. 1; and

DETAILED DESCRIPTION OF THE PREFERRED EMBODIMENTS

Figure 3:
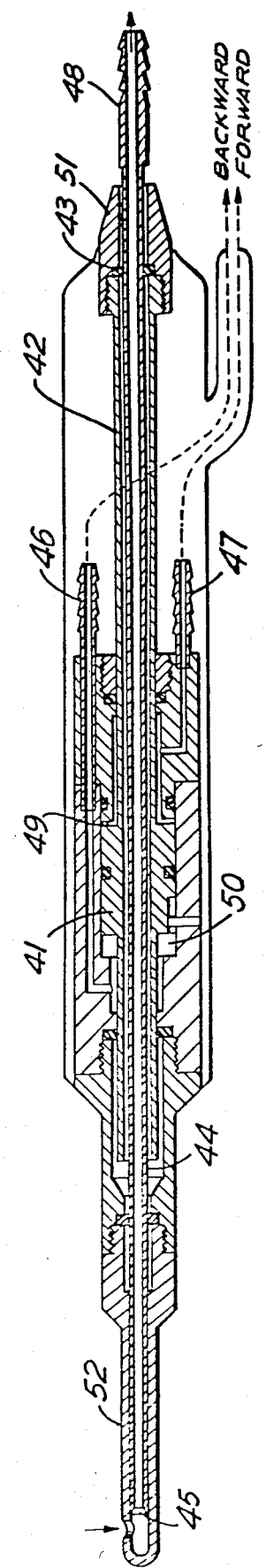
FIG. 3 is a sectional view of a vitreous cutter usable with the control system according to the invention.

Referring now to FIG. 1, the high pressure gas supply comprises a cylinder 1 which is of the nonsyphon type and holds a compressed gas such as $N_2O$ or $CO_2$ which is held at its natural gas pressure at ambient temperature. This pressure, which is about 750 psi at room temperature, is connected through the gas input connector 2 through a pressure line having a safety valve 3 thereon which vents to the atmosphere when the pressure exceeds 1000 psi. A pressure gauge may be employed at the safety valve to indicate the current pressure at the line.

A pressure reducer 4 is optionally provided where such is required by law and this drops the pressure from 750 psi to approximately 150 psi, which is still many times higher than the pressure utilized by conventional control systems (from 10 to 20 psi).

The gas input means provides the safety factors of having a safety valve connected close to the input which automatically vents gas to the atmosphere if the gas pressure exceeds a predetermined amount. This avoids the risk of explosion in the case where the pressure of the gas exceeds the mechanical strength of the pneumatic components.

The use of compressed gas has advantages over the use of compressors which are noisy and need technical assistance for proper operation and are frequently defective. Moreover, gases such as $N_2O$ are readily available because this gas is also used in anesthesia by surgeons.

The gas from the pressure reducer 4 is fed to the input of a one-way valve 5 which is actuated by solenoid 6 under the control of control circuit 20 which will be explained hereinafter. Valve 5 is connected via line a to one-way valve 7 which is controlled by solenoid 8 via control circuit 20. Valve 7 has its output vented to the atmosphere via line b as shown.

At the series connection between valves 5 and 7 the pneumatic line is tapped by line c which is connected to the input of five-way valve 9 which is actuated by solenoid 10 which, in turn, is controlled by control circuit 20.

Five-way valve 9 has two outputs connected to lines e and f which are adapted to connecting to a vitreous cutter, and two outputs connected to lines d and g which are connected to throttlers 11 and 12, respectively, and which are vented to the atmosphere as shown.

Five-way valve 9 has two states, a first state wherein, as shown, input line c is in communication with output line f and line e is vented to the atmosphere via output line d, and a second state wherein input line c is in communication with output line e and line f is in communication with line g and vented to the atmosphere via throttler 12.

Referring now to FIG. 2, the control circuit 20 is shown in more detail.

Control circuit 20 includes switch 13 which when in the open state as shown, maintains indicator lamp 14 in the off position and controls solenoids 6 and 8 through inverter 34 and solenoid drive circuits 35 and 36 which are conventional drive circuits. In the state shown, solenoid driver 35 due to the inversion by inverter 34, maintains one-way valve 5 in the closed state while driver 36 maintains one-way valve 7 in the open state. As a result, whichever state the five-way valve is in at the time, the one-way valve 5 blocks the pressure from the gas input means and at the same time whichever cutter line e or f is connected to line c, will be vented through one-way valve 7 and line b to the atmosphere. The other output of lines e and f will be connected via a throttler 11 or 12 to the atmosphere and thus all of the lines are vented and there is no residual pressure build-up in the system in the off state. Switch 13 is a microswitch positioned at the console connection to lines e and f to which the vitreous cutter is to be connected and is operated to the closed state when lines e and f are connected to lines 46 and 47 Switch 13 is thus open when a vitreous cutter is not connected to the system console which houses the electronic circuitry and is closed when the vitreous cutter is connected to the unit. The open state of switch 13 enables a logic 1 to be applied to one input of NOR-gate 29 which effectively inhibits any actuation of solenoid 10 by the gate circuitry, which will be described hereinafter.

The control circuit also includes circuitry for effecting either a single step mode for the five-way valve 9 or a repetitive mode therefor which effect a single step and repetitive mode for the connected cutter. These modes are effected by variable frequency generator 25 which is a conventional off-the-shelf circuit such as an NE555 timing generator which has a potentiometer 21 connected to the input thereof for varying the frequency output thereof. The output of frequency generator 25 is fed to a divider 26 to obtain the proper range of frequencies to be used in connection with a vitreous cutter. The output of divider 26 is applied to one input of NOR-gate 28 which permits the square wave output of divider 26 to be passed therethrough if enabled. The enabling or inhibiting of gate 28 is effected by the selection of the single or repetitive modes by push-buttons 22 and 23 respectively which have their outputs applied to either side of flip-flop 27. When the repetitive mode is desired, push-button 23 is depressed, setting flip-flop 27 in the state wherein a logic 0 is applied to the other input of NOR-gate 28. The logic 0 input effectively enables the gate to pass whatever signal is applied to the other input thereof, to wit, the square wave from divider 26. On the other hand, when a single step mode is to be desired, push-button 22 is depressed which sets flip-flop 27 in the other mode wherein a logic 1 is applied to the other input of NOR-gate 28. This effectively inhibits the output of the gate such that a logic 0 always occurs at the output thereof and is applied to gate 29.

NOR-gate 29 passes the output from NOR-gate 28 when switch 13 is closed and thus switch 13 effectively disables any actuation when a cutter is not connected to the control system. The output of NOR-gate 29 is fed to the inputs of NOR-gate 30 and AND-gate 31 which are used, in conjunction with push-button switch 24, to control the initial position of five-way valve 9 in the single step mode. When switch 24 is in the open state as shown, a logic 0 is applied to the inputs of NOR-gate 30 and AND-gate 31 thus effectively inhibiting the output of AND-gate 31 and enabling NOR-gate 30 to pass the output of NOR-gate 29. This output from gate 30 is then passed through NOR-gate 32 which has the other input thereof at logic 0 from AND-gate 31 and solenoid 10 is effectively driven through conventional driver 33 to continuously and repetitively actuate five-way valve 9 so that it passes from one state to the other.

When one places the system into the single step mode by depression of push-button 22, it may then be desired to initially maintain the pressure applied to the cutter either at output line e or output line f. This is carried out by the "open" and "close" switch 24.

When the push-button 24 is depressed, a logic 1 will be applied to the inputs of gates 30 and 31. Since gate 31 will have logic 1 applied to both inputs thereof, the output thereof will be a logic 1 which, when applied to the input of gate 32, will result in logic 0 output. In this condition, solenoid driver 33 actuates solenoid 10 to place the five-way valve 9 in the second state wherein pressure line c is in communication with output line e. As a result of the proper connection of the cutter to lines e and f, this will effect the moving of the blade backwards so as to open the tip and will stay there to effect this as the starting position. When the button is released, a logic 0 will be applied to gates 30 and 31 effecting a logic 1 output from NOR-gate 32. This stores valve 9 to the position shown thus moving the blade forward again where it will stay. Thus the cutting cycle can be effected either in the forward or the backward direction.

NOR-gate 32 also has a third input connected to foot actuated switch 37. When the switch 37 is in the non-actuated state, no energization of the solenoid 10 will occur. Upon depression of the foot actuated switch 37, gate 32 will enable all of the above mentioned modes to take place.

FIG. 3 shows a vitreous cutter for use with the control system according to the invention.

As shown, the vitreous cutter has two input lines 46 and 47, with input line 46 connected to line e and input line 47 connected to line f of the control system shown in FIG. 1. The application of pressure to line e causes the blade 44 to move backward due to the pressure applied on the forward face of piston 41 in cylinder chamber 50. Line 47 on the other hand effects the forward movement of blade 44 by applying the pressure through line f to the other face of piston 41 in cylinder chamber 49.

In the cutter shown, the piston 41 is mechanically connected to blade 44 via the threaded cap 51 and O-ring 43. The blade 44 has one end portion 48 connected to a suction source such as a syringe or the like and the other end 45 extending through the threaded tip 52 which, in connection with sharpened end point 45 of blade 44, effects the cutting action. While the cutter shown herein is a push-type cutter wherein the cutting action occurs when the blade is moved forward, it is clear that a pull type blade can also be utilized due to the versatility of the control system.

It will be appreciated that the instant specification and claims are set forth by way of illustration and not limitation, and that various modifications and changes may be made without departing from the spirit and scope of the present invention. For example, any source of compressed gas ranging between 150-750 p.s.i. may be used as the gas supply, such as compressed air.

What is claimed is:

1. A surgical device including a control system of the type having two alternately energized power lines, said device comprising a housing having a central passage and a piston chamber, a cutting member reciprocally mounted in said passage, a piston in said piston chamber connected to said cutting member, a first and second air path adapted to be connected to respective ones of said alternately energized power lines to control movement of the piston, said first air path communicating with said piston chamber on one side of said piston and said second air path communicating with said piston chamber on the other side of said piston, whereby the reciprocation of said cutting member is controlled by the alternate application of air to the opposite ends of said piston, said control system including gas input means receptive of a supply of high pressure gas, first and second actuable one-way valves connected in series with the gas input means, with the input of the first valve connected to the output of the gas input means and the output of the second valve vented to the atmosphere, wherein each valve is actuable between a closed state and an open state wherein the input and output are in communication; five-way actuatable valve means for controlling the flow of a fluid having an input connected to the series connection between the first and second valves, two outputs vented to the atmosphere and two outputs connectable to said surgical device, wherein the valve means is actuable between a first state wherein the input is in communication with one device output and the other device output is in communication with one venting output and a second state wherein the input is in communication with the other device output and the one device putput is in communication with the other venting output; control means for maintaining the first and second valves in the closed and open states respectively and responsive to the connection of said device to said control system for thereafter reversing said states and for selectively actuating the five-way valve means between the first and second states only when the first valve is open and the second valve is closed and wherein said first and second air paths of said surgical device are connectable to said five-way valve means such that said cutting member is affected by the alternate application of high pressure gas to said first and second air paths.

* * * * *